US006346610B1

(12) United States Patent
Kataoka et al.

(10) Patent No.: US 6,346,610 B1
(45) Date of Patent: Feb. 12, 2002

(54) PROCESS FOR PREPARING ANTIFUNGAL V-28-3M

(75) Inventors: Noriyasu Kataoka, Kanagawa; Kenzo Tanaka, Mie; Masanobu Yatagai, Kanagawa, all of (JP)

(73) Assignee: Ajinomoto Co., Ltd., Tokyo (JP)

( * ) Notice: Subject to any disclaimer, the term of this patent is extended or adjusted under 35 U.S.C. 154(b) by 0 days.

(21) Appl. No.: 09/445,240

(22) PCT Filed: Jun. 2, 1998

(86) PCT No.: PCT/JP98/02439

§ 371 Date: Dec. 3, 1999

§ 102(e) Date: Dec. 3, 1999

(87) PCT Pub. No.: WO98/55492

PCT Pub. Date: Oct. 12, 1998

(30) Foreign Application Priority Data

Jun. 3, 1997 (JP) .............................................. 9-145249

(51) Int. Cl.⁷ ................................................ C07M 1/00
(52) U.S. Cl. ....................................... 536/6.5; 536/18.5
(58) Field of Search ................................. 536/6.5, 18.5

(56) References Cited

U.S. PATENT DOCUMENTS 4,235,993 A * 11/1980 Sipos et al. .................. 536/6.5

FOREIGN PATENT DOCUMENTS

| EP | 285805 | 10/1988 |
|----|--------|---------|
| JP | 50-129531 | 10/1975 |
| JP | 1-56683 | 3/1989 |
| JP | 4-145066 | 5/1992 |
| WO | WO 88/00201 | 1/1988 |
| WO | WO 88/02004 | 3/1988 |

* cited by examiner

*Primary Examiner*—Elli Peselev
(74) *Attorney, Agent, or Firm*—Oblon, Spivak, McClelland, Maier & Nuestadt, P.C.

(57) ABSTRACT

An industrially suitable process for preparing V-28-3M useful as an antimycotic agent by conducting methyl esterification of V-28-3 efficiently. V-28-2 is efficiently converted into V-28-3M by protecting the amino group of the amino sugar of V-28-3 with an appropriate protecting group, subjecting the carboxyl group of V-28-3 to methyl esterification with methyl methanesulfonate or methyl p-toluenesulfonate in the presence of a base, and deprotecting the N-protected intermediate.

1 Claim, 8 Drawing Sheets

CHEMICAL SHIFT

PROCESS FOR PREPARING ANTIFUNGAL V-28-3M

TECHNICAL FIELD

The present invention relates to a process for preparing V-28-3M useful as an antimycotic agent, and to an intermediate thereof.

BACKGROUND ART

In recent years, mycotic opportunistic infectious disease and deep mycosis are apt to increase due to the improvement of longevity with the progress in advanced medical care and the like. Most of the heptaene antimycotic agents generally used for these mycoses have strong toxicity for animal cells in addition to their antimycotic activities. Accordingly, an antimycotic agent having low cytotoxicity has been expected.

A novel heptaene antimycotic agent, V-28-3M, having high antimycotic activity and low toxicity for animal cells has been found (JP-A-63-218686 and JP-A-3-81225). V-28-3M is obtained by subjecting V-28-3 which is also a heptaene antimycotic agent (JP-A-61-189224 and JP-A-2-300134) to methyl esterification.

Previously, this methyl esterification was carried out using diazomethane or trimethylsilyldiazomethane. However, diazomethane is explosive and has a markedly strong toxicity. On the other hand, trimethylsilyldiazomethane as its substituent agent is expensive, so that the use of each of these reagents is not suitable for an industrially appropriate method as methyl esterification.

As an agent for methyl esterification other than diazomethane and trimethylsilyldiazomethane, methyl iodide can be exemplified which has been reported in relation to the methyl esterification of amphotericin B. However, when V-28-3 is directly subjected to methyl esterification with methyl iodide, a compound in which the amino group of the amino sugar is multiply methylated is formed as the main product, so that the yield of V-28-3M as the objective product becomes extremely low.

Furthermore, when an N-protected form of the amino group of the amino sugar of V-28-3 (hereinafter referred to as "N-protected V-28-3") is subjected to methyl esterification with methyl iodide, the formation ratio of an N-protected form of by-product D (a side reaction product which gives a retention time of 20 minutes under the analyzing conditions shown in Examples, a mono-methylation product of the aromatic amino group of V-28-3M) is considerably increased. This N-protected by-product D is converted into by-product D via a deprotection step of the protecting group. The by-product D is hardly reduced by the purification step. Thus, when methyl iodide is used as the methyl esterification agent in methyl esterification of the N-protected V-28-3, contamination of impurity (by-product D) in the medicinal material is increased, so that such a method is not suitable as a production process of medicaments.

DISCLOSURE OF THE INVENTION

An object to be solved by the present invention is to develop an industrially suitable method for preparing V-28-3M by subjecting V-28-3 to methyl esterification efficiently. At the same time, development of its production process with low by-production of impurities is expected.

With the aim of attaining the above-described object, the present inventors have conducted intensive studies and found, as a result of the efforts, a method which can inhibit by-production of the by-product D and efficiently convert V-28-3 into V-28-3M, by protecting the amino group of the amino sugar of V-28-3 with an appropriate protecting group, subjecting the carboxyl group of the N-protected V-28-3 to methyl esterification with methyl methanesulfonate or methyl p-toluenesulfonate in the presence of a base, and deprotecting the N-protected intermediate.

On the other hand, when unprotected V-28-3 is directly treated with methyl iodide, methyl methanesulfonate or methyl p-toluenesulfonate in the presence of a base, the yield of the objective product is low and a compound in which the amino group of the amino sugar moiety is multiply methylated is formed as the main product in addition to the objective product.

Also, when methyl esterification is carried out with methyl iodide under basic conditions using the N-protected intermediate of an appropriate amino sugar, N-protected by-product D is formed in an amount of approximately 5 to 10 area % (per N-protected V-28-3M, HPLC analysis) in addition to the objective N-protected V-28-3M. The N-protected by-product D formed under the reaction conditions remains in the final product in an amount of 6 to 8 area % (per V-28-3M, HPLC analysis) as the by-product D after the subsequent deprotection step and purification step.

On the other hand, when the N-protected intermediate is subjected to methyl esterification using methyl methanesulfonate or methyl p-toluenesulfonate as the methyl esterification agent, formation of the N-protected by-product D can be reduced to about 1 area % or less (per N-protected V-28-3M, HPLC analysis). The N-protected by-product D is reduced to its detection limit or less as the by-product D in the final product after the subsequent deprotection step and purification step.

Accordingly, the present invention relates to a process for preparing V-28-3M represented by formula (4), comprising reacting an N-protected form of V-28-3 represented by formula (1) (wherein $R^1$ represents a hydrogen atom, and X represents formula (2) or (3)) with methyl methanesulfonate or methyl p-toluenesulfonate in the presence of a base for methyl esterification of the carboxyl group of the N-protected compound to produce a methyl ester of N-protected V-28-3 represented by formula (1) (wherein $R^1$ represents a methyl group, and X represents formula (2) or formula (3)), and releasing the N-protecting group from the protected intermediate, and to a methyl ester of the N-protected V-28-3 represented by formula (1) (wherein $R^1$ represents a methyl group, and X represents formula (2) or formula (3)).

Formula (1):

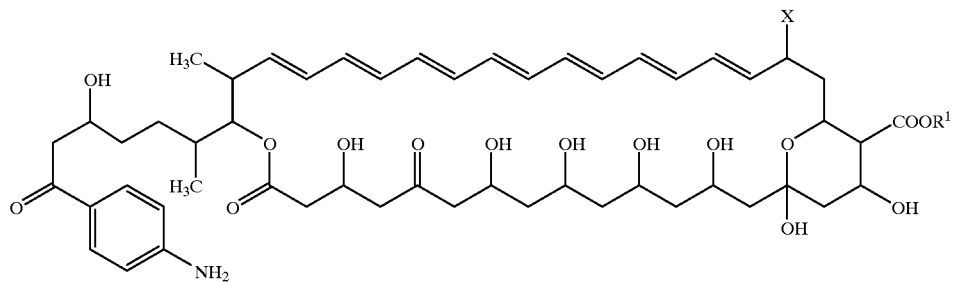

Formula (2):

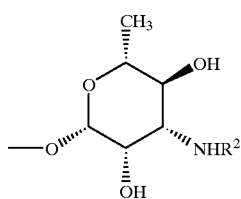

($R^2$ represents a 9-fluorenylmethoxycarbonyl group or a trifluoroacetyl group)

Formula (3):

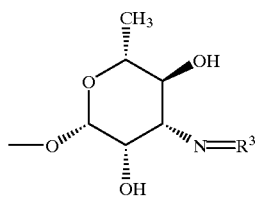

($R^3$ represents a benzylidene group)

Formula (4):

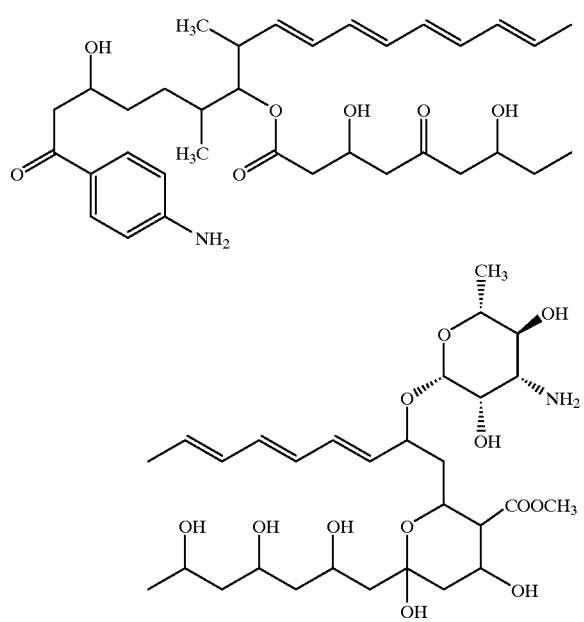

BEST MODE FOR CARRYING OUT THE INVENTION

Figure 1:
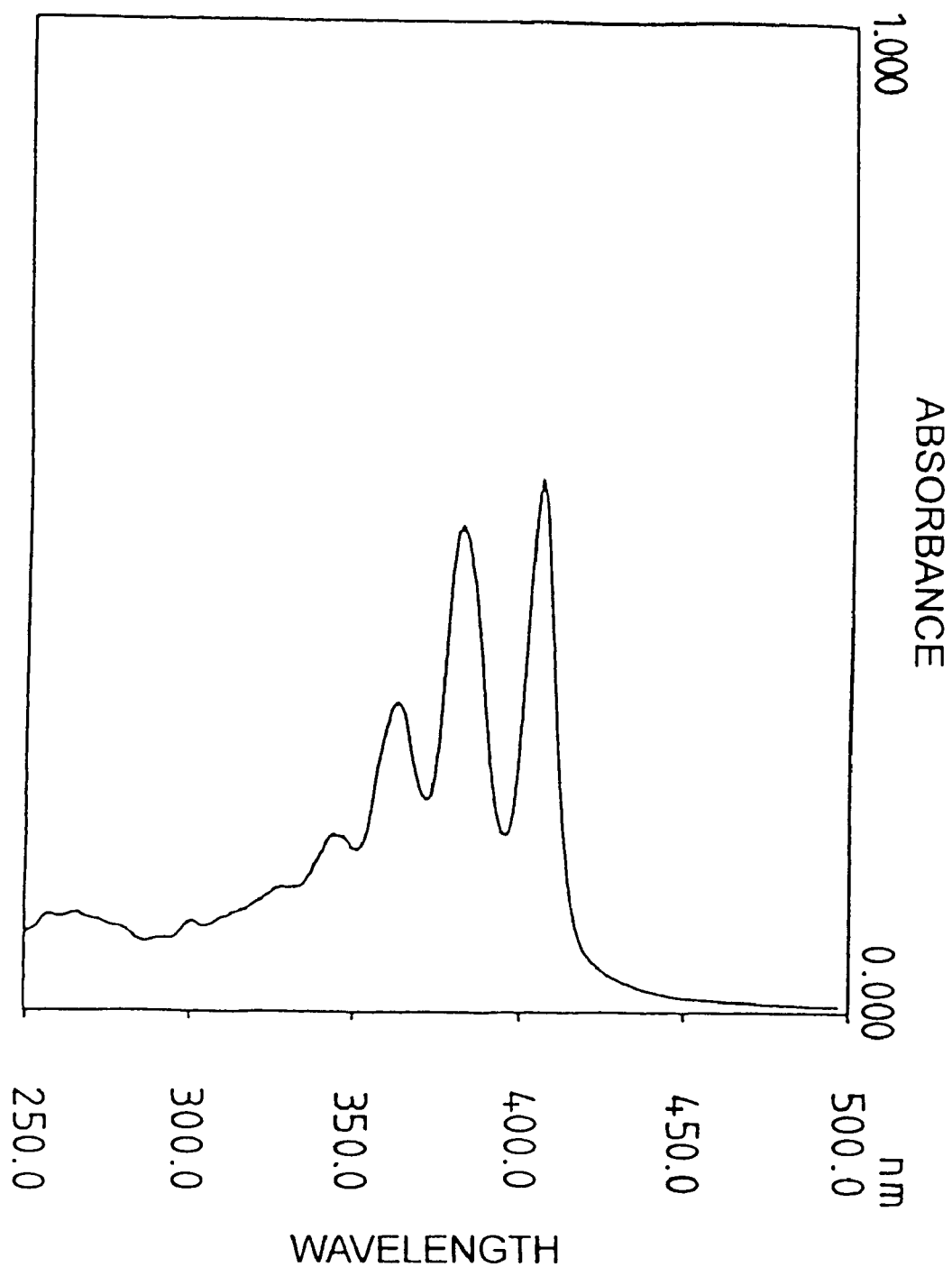
FIG. 1 is a graph showing ultraviolet region absorption spectrum of N-(9-fluorenylmethoxycarbonyl)-V-28-3 obtained in Example 1.

A 9-fluorenylmethoxycarbonyl group (hereinafter referred to as "Fmoc") and a trifluoroacetyl group can be exemplified as proper groups of the protecting group $R^2$ of the amino group of the amino sugar of formula (2) and a benzylidene group can be exemplified as a proper group of the protecting group $R^3$ of the amino group of the amino sugar of formula (3). Introduction of these protecting groups can be carried out by generally known methods. Since these protecting groups can be deprotected under relatively mild conditions, they are markedly advantageous for a compound, such as V-28-3M, which is unstable under acidic and basic conditions.

For example, a 9-fluorenylmethoxycarbonyl group can be introduced by reacting V-28-3 with a 9-fluorenylmethoxycarbonylation reagent, such as N-(9-fluorenylmethoxycarbonyloxy)succinimide or the like, at 10 to 30° C., preferably 15 to 25° C., for 30 minutes to 3 hours in dimethylformamide, dimethyl sulfoxide (hereinafter referred to as "DMSO") or a mixed solvent thereof with an alcohol or the like, preferably in a mixed solvent of methanol/dimethyl sulfoxide.

A trifluoroacetyl group can be introduced by reacting V-28-3 with a trifluoroacetylation reagent, such as ethyl trifluoroacetate or the like, at 10 to 30° C., preferably 15 to 25° C., for 15 to 25 hours in the presence of a base, such as diisopropylethylamine or the like, in dimethylformamide, dimethyl sulfoxide or a mixed solvent thereof with an alcohol or the like, preferably in a mixed solvent of methanol/dimethyl sulfoxide.

A benzylidene group can be introduced by reacting V-28-3 with benzaldehyde at 10 to 30° C., preferably 15 to 25° C., for 0.5 to 2 hours in a solvent, such as dimethyl sulfoxide, dimethylformamide or the like, preferably dimethyl sulfoxide.

The methyl esterification of the N-protected V-28-3 obtained by the above-described method can be carried out by reacting the compound with methyl methanesulfonate or methyl p-toluenesulfonate at 5 to 30° C., preferably 5 to 25° C., for 4 to 20 hours, preferably 4 to 8 hours, in the presence of a base, such as potassium carbonate, diisopropylethylamine or the like, in dimethylformamide, dimethyl sulfoxide or a mixed solvent thereof with an alcohol or the like, preferably in a mixed solvent of methanol/dimethyl sulfoxide.

The deprotection reaction of the thus obtained V-28-3M protected with a 9-fluorenylmethoxycarbonyl group or a trifluoroacetyl group can be carried out under basic conditions. For example, the protecting group of N-(9-fluorenylmethoxycarbonyl)-V-28-3M can be removed using a base, such as aqueous ammonia, piperidine or 1,8-diazabicyclo[5.4.0]undec-7-ene (DBU), in a mixed solvent, such as methanol/dimethyl sulfoxide or the like.

Furthermore, the deprotection reaction of the V-28-3M protected with a trifluoroacetyl group can be carried out in a mixed solvent, such as methanol/dimethyl sulfoxide, using a base, such as aqueous ammonia or an aqueous potassium carbonate solution.

Also, the V-28-3M protected with a benzylidene group is easily deprotected under acidic conditions, for example, in a phosphate buffer of pH 4.0, to give v-28-3M.

The following describes the present invention in detail with reference to examples. The present invention is not restricted by these examples.

EXAMPLES

Crude V-28-3 for use in Examples was prepared in accordance with the method in examples described in JP-B-4-32836. Also, only typical signals were shown in the following Examples regarding the $^1$H-NMR data, and reaction solutions were analyzed using HPLC under the following conditions.

<HPLC Analysis Conditions>
Column Used
   Reverse phase ODS silica gel column (YMC-Pack; ODS-AM312), column size 6.0 mm in inner diameter×150 mm in length, S-5
Column temperature: 25° C.
Eluting Solution
   Solution A): aqueous solution of 50 mM sodium dihydrogenphosphate (adjusted to pH 4.0)
   Solution B): acetonitrile for HPLC analysis
Gradient Program
   (Solution A/Solution B)=initial composition (60/40)—after 13 minutes (60/40)—after 23 minutes (40/60)—after 35 minutes (40/60)
Column Flow Rate: 1.0 ml/min
Detector: UV 360 nm
Sample injected: 10 µl Example 1

Preparation of N-(9-fluorenylmethoxy-carbonyl)-V-28-3

In 2.4 L of a dimethyl sulfoxide/methanol (mixing ratio 9:2, volume ratio) solution, 37.38 g of crude V-28-3 (22.92 mmol) was dissolved, and N-(9-fluorenylmethoxycarbonyloxy)succinimide (38.3 g) was added thereto at room temperature by dividing it into 4 portions. This reaction solution was stirred at room temperature for 2 hours and then cooled in an ice bath, and 2.4 L of water was added dropwise thereto over 1 hour to obtain a slurry of the thus precipitated title compound. The title compound was separated from the slurry and washed with 300 ml of water and 500 ml of methanol, and then the crude precipitate was separated and dried to obtain 49.28 g of crude crystals of the title compound with a yield of 94%. The crude crystals were used in the following methyl esterification without purification.

Figure 2:
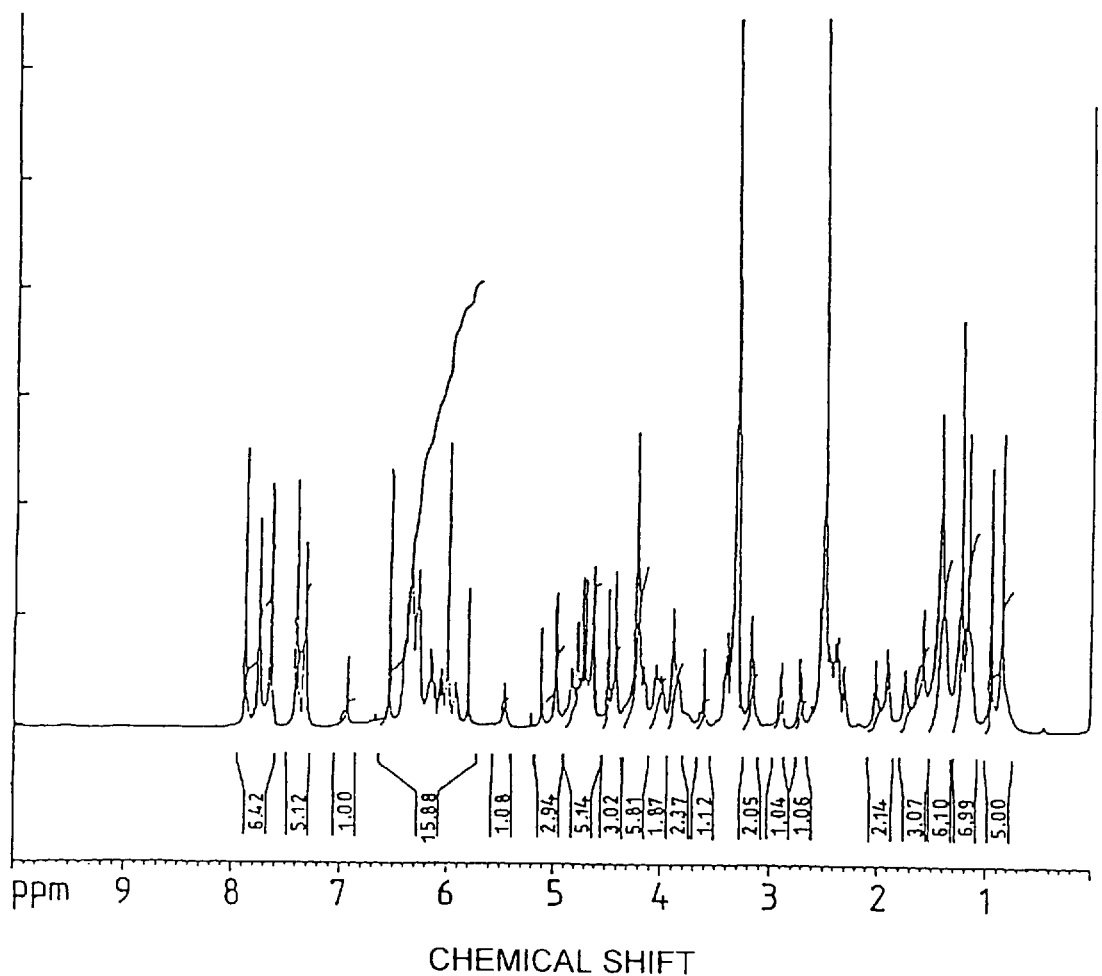
FIG. 2 is a graph showing $^1$H-NMR spectrum of N-(9-fluorenylmethoxycarbonyl)-V-28-3 obtained in Example 1.

Also, a purified product of this compound for use in the measurement of its physicochemical data was prepared in the following manner. That is, a reaction solution containing N-(9-fluorenylmethoxycarbonyl)-V-28-3 was prepared under the conditions described in Example 1 and directly purified by silica gel column chromatography, the eluted fraction containing the title compound was concentrated under a reduced pressure, five volumes of water was added to the concentrated solution under ice cooling, and then the thus precipitated partially purified heavy liquid was separated by centrifugation and dried. The thus obtained partially purified yellow product was purified by reverse phase HPLC (column: YMC-Pack ODS-AM312, 150×6.0 mm I.D., mobile phase: 50 mM ammonium acetate buffer (pH 4.0)/acetonitrile=40/60) and a yellow solid was recovered to obtain a purified product of the title compound having the following physicochemical properties.
1) Appearance: yellow powder
2) Mass spectrometry: MS (FAB+); m/z 1335.8 (MH$^+$)
3) Ultraviolet absorption spectrum (measured in MeOH): shown in FIG. 1
   λmax 363, 382, 405
4) $^1$H-NMR (measured in DMSO-d$_6$): shown in FIG. 2
   δ7.89 ppm (d, J=7.56 Hz, aromatic-H), 7.76, 7.65, 7.42, 7.34, 6.93 (m, Fmoc-group), 6.55 (d, J=8.59, aromatic-H)

Example 2

Preparation of N-(9-fluorenylmethoxycarbonyl)-V-28-3M (Method 1)

In 700 ml of a dimethyl sulfoxide-methanol (mixing ratio 9:2, volume ratio) solution, 13.5 g of crude N-(9-fluorenylmethoxycarbonyl)-V-28-3 (9.5 mmol) obtained by the method in Example 1 was dissolved at room temperature. To this solution, 7.2 ml of methyl p-toluenesulfonate and 1.3 g of potassium carbonate were added, followed by stirring at 25° C. for 4 hours. The reaction solution was cooled to 5√ C. and stirred overnight to obtain a reaction solution containing 11.9 g of the title compound with a yield of 93%. The title compound was used in the following deprotection reaction step without isolating it from the solution.

In this method, the formation ratio of the Fmoc-protected by-product D was 0.86% by area ratio (per Fmoc V-28-3M, HPLC analysis) which was lower than that of the case in which methyl iodide was used as the methyl esterification agent (see Comparative Example 1 shown below).
(Method 2)

Methyl esterification of 52 mg (0.033 mmol) of crude N-(9-fluorenylmethoxycarbonyl)-V-28-3 obtained by the method in Example 1 was carried out under the same conditions of the method 1 in Example 2, except that methyl methanesulfonate was used instead of methyl p-toluenesulfonate as the methyl esterification agent, to obtain a reaction solution containing 38 mg of the title compound with a yield of 86%.

Figure 3:
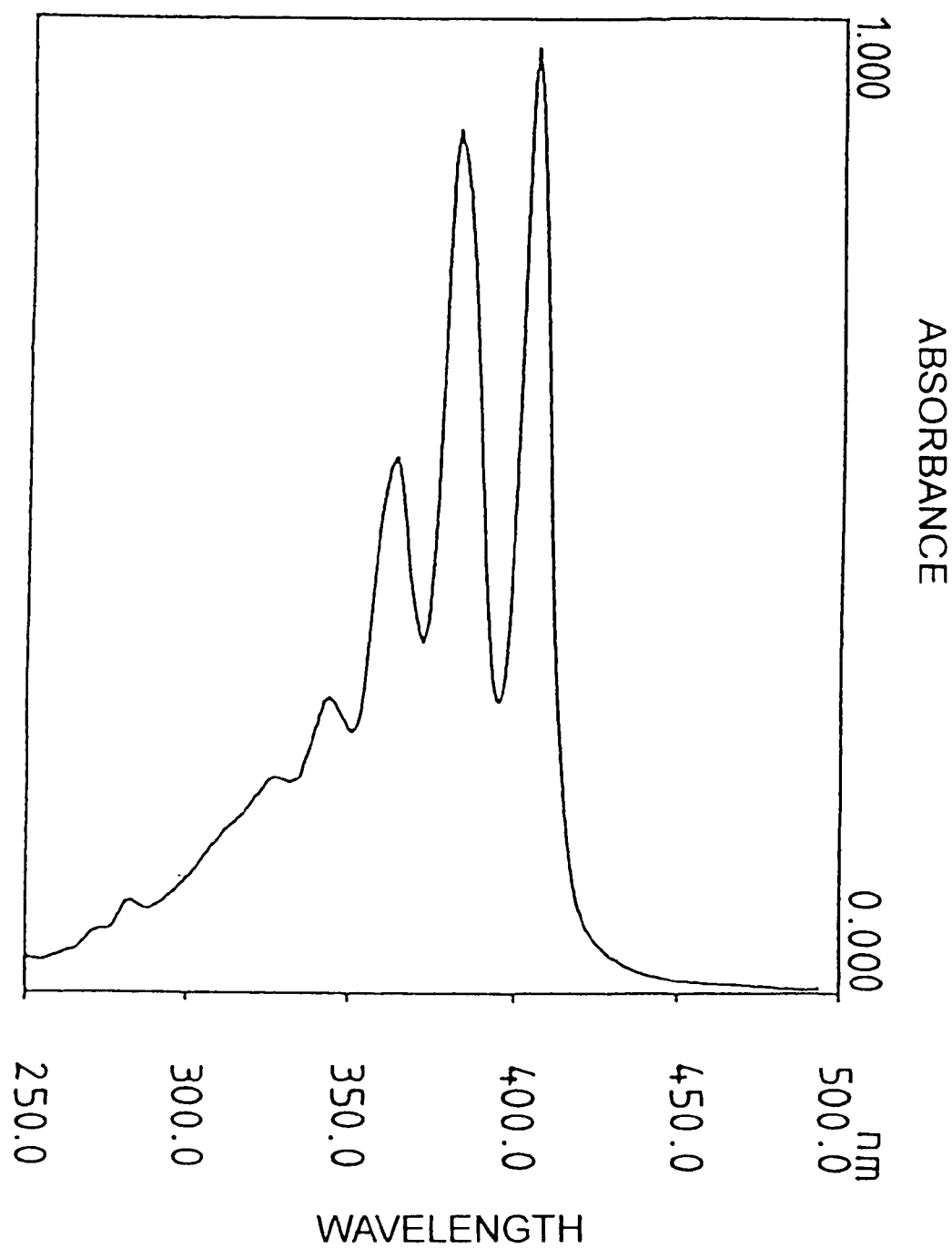
FIG. 3 is a graph showing ultraviolet region absorption spectrum of N-(9-fluorenylmethoxycarbonyl)-V-28-3M obtained in Example 2.
Figure 4:
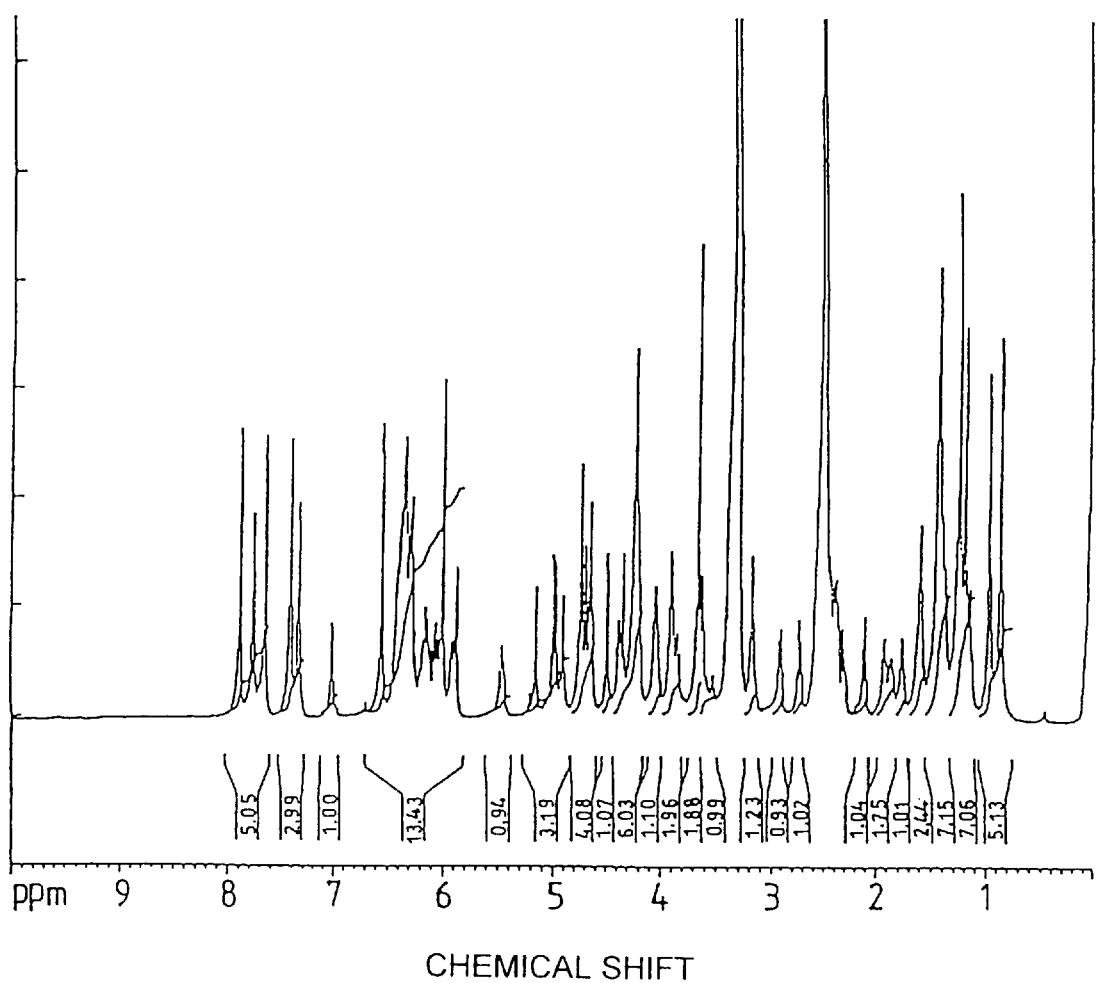
FIG. 4 is a graph showing $^1$H-NMR spectrum of N-(9-fluorenylmethoxycarbonyl)-V-28-3M obtained in Example 2.

A purified product of the title compound for use in the measurement of its physicochemical data was prepared in the following manner. That is, the same volume of water was added to the above reaction solution under ice-cooling to precipitate the title compound, and the precipitate was recovered by centrifugation and dried. The thus obtained brown solid was purified by silica gel chromatography, the eluted fraction containing the objective compound was concentrated, and then five volume of water was added to the concentrated solution under ice cooling to precipitate the objective compound. The resulting precipitate was recovered by centrifugation and dried. The thus obtained partially purified yellowish brown product was purified by reverse phase HPLC under the separation conditions shown in Example 1 to obtain a purified product of the title compound having the following physicochemical properties.
1) Appearance: yellow powder
2) Mass spectrometry: MS (FAB+); m/z 1349.7 (MH$^+$)
3) Ultraviolet absorption spectrum (measured in MeOH): shown in FIG. 3
   λmax 363, 381, 405
4) $^1$H-NMR (measured in DMSO-d$_6$): shown in FIG. 4
   δ7.90 ppm (d, J=7.52 Hz, aromatic-H), 7.77, 7.65 7.42, 7.33, 7.01 (m, Fmoc-group), 6.45 (d, J=8.21 ), 3.65 (s, methyl ester)

Example 3

Preparation of N-trifluoroacetyl-V-28-3

Crude V-28-3 (204 mg, 0.09 mmol ) was dissolved in a dimethyl sulfoxide (4.35 ml )-methanol (0.65 ml ) solution, and 0.16 ml of dissopropylethylamine and subsequently 0.11 ml of ethyl trifluoroacetate were added thereto at room temperature, followed by stirring overnight at 20° C. to obtain a reaction solution containing 96.6 mg of the title compound with a yield of 91%. The thus obtained compound was directly used as the reaction solution in the methyl esterification without purification.

Figure 5:
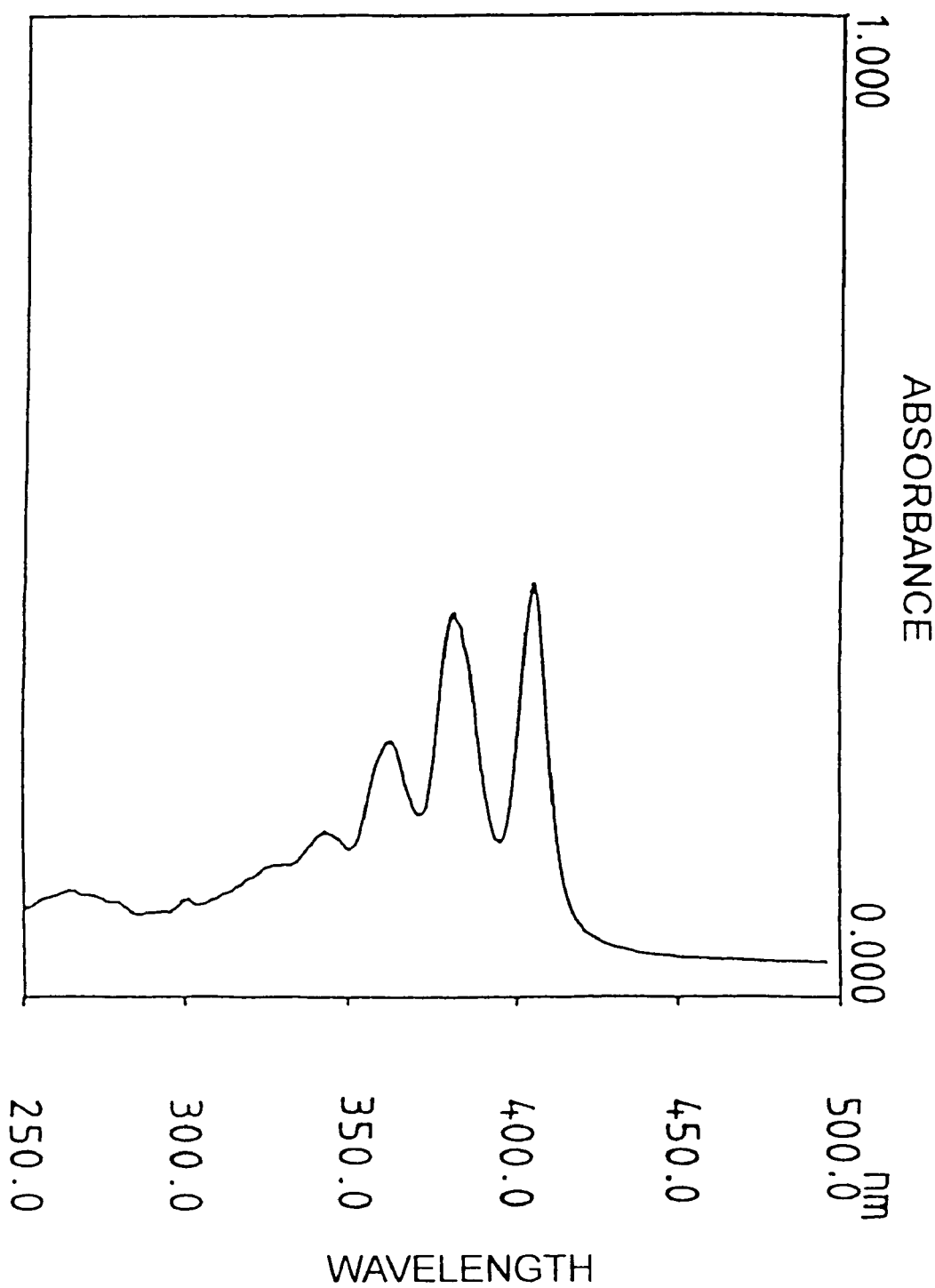
FIG. 5 is a graph showing ultraviolet region absorption spectrum of N-trifluoroacetyl-V-28-3 obtained in Example 3.
Figure 6:
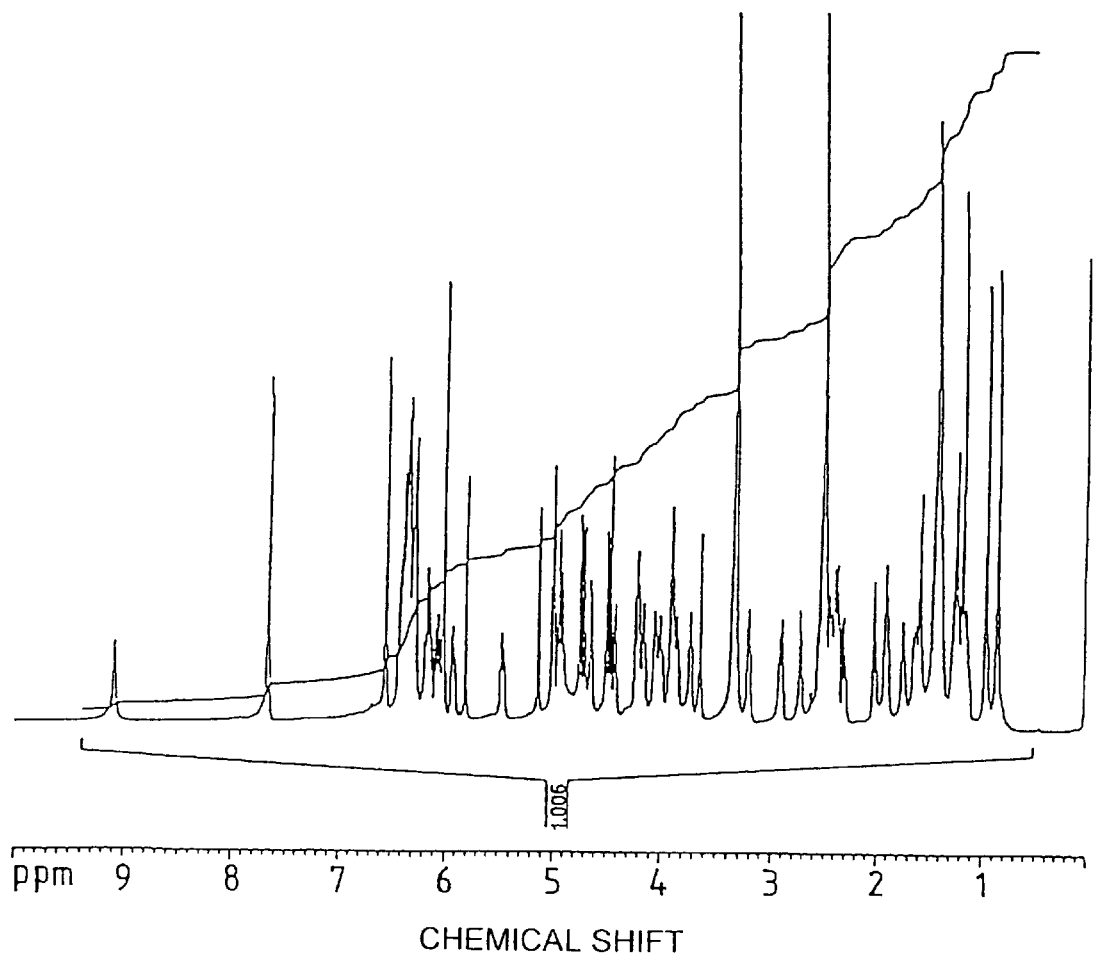
FIG. 6 is a graph showing $^1$H-NMR spectrum of N-trifluoroacetyl-V-28-3 obtained in Example 3.

Also, the title compound was isolated and purified in the following manner. That is, the reaction solution was added to 20 volumes of diethyl ether, and the thus obtained heavy liquid of the crude product was separated by decantation and dried under a reduced pressure. The thus obtained crude brown product was purified by reverse phase HPLC under the same conditions shown in Example 1 to obtain a purified product of the title compound having the following physicochemical properties.
1) Appearance: yellow powder
2) Mass spectrometry: MS (FAB+); m/z 1209.5 (MH$^+$)
3) Ultraviolet absorption spectrum (measured in MeOH): shown in FIG. 5
   λmax 363, 382, 405
4) $^1$H-NMR (measured in DMSO-d$_6$): shown in FIG. 6
   δ9.10 ppm (bs), 7.60 (d, J=8.6 Hz, aromatic-H), 6.6 (d, 2 H, J=8.5, aromatic-H)

Example 4

Preparation of N-trifluoroacetyl-V-28-3M

To 5 ml of a dimethyl sulfoxide-methanol mixed solvent (mixing ratio 9/2) containing 100 mg (0.08 mmol) of N-trifluoroacetyl-V-28-3 obtained by the method in Example 3, 75 mg of methyl p-toluenesulfonate and 11 mg of potassium carbonate were added at 5° C., and the resulting reaction solution was returned to room temperature and stirred overnight. A reaction solution containing 88 mg of the title compound was obtained with a yield of 90%. This compound was subjected to the subsequent step without separation.

Figure 7:
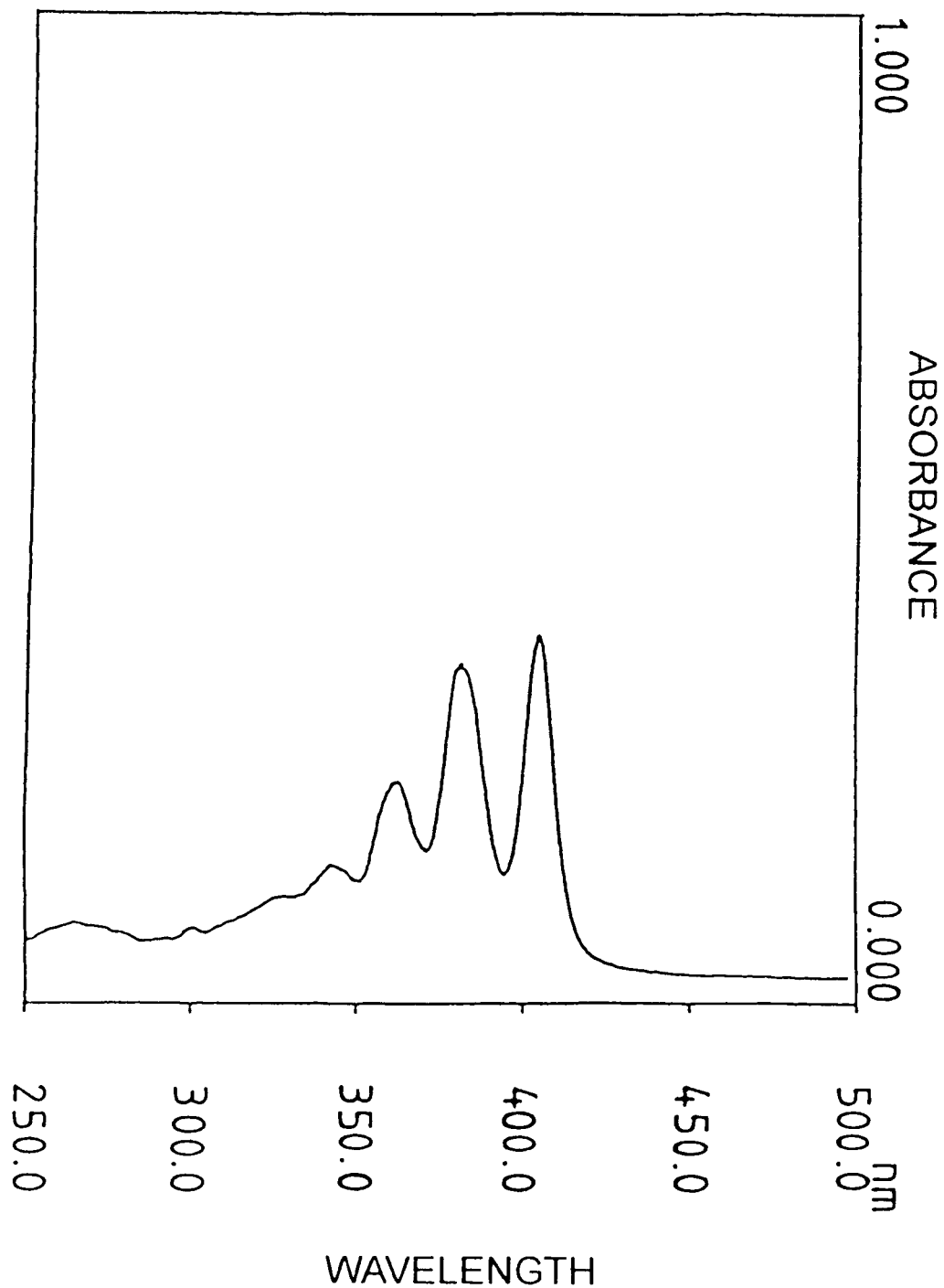
FIG. 7 is a graph showing ultraviolet region absorption spectrum of N-trifluoroacetyl-V-28-3M obtained in Example 4.
Figure 8:
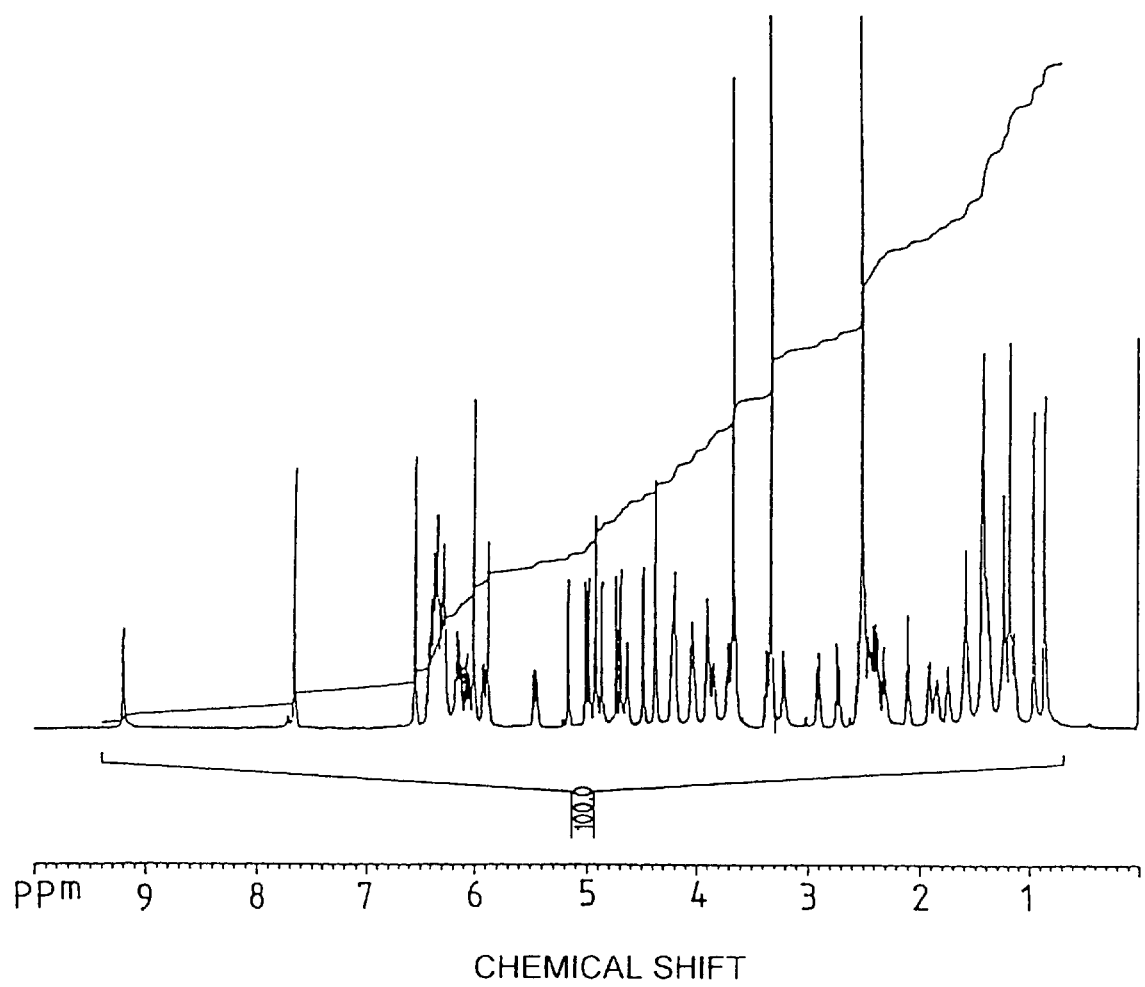
FIG. 8 is a graph showing $^1$H-NMR spectrum of N-trifluoroacetyl-V-28-3M obtained in Example 4.

The title compound was isolated and purified in the following manner. That is, the above-described reaction solution was added to 3 volumes of water under ice cooling, and the thus obtained heavy liquid of the crude product was recovered by centrifugation and dried under a reduced pressure. The crude brown product obtained in this manner was purified by silica gel column chromatography, and the thus obtained partially purified product was purified by reverse phase HPLC under the same conditions in Example 1 to obtain a purified product of the title compound having the following physicochemical properties.
1) Appearance: yellow powder
2) Mass spectrometry: MS (FAB+); m/z 1223.6 (MH$^+$)
3) Ultraviolet absorption spectrum (measured in MeOH): shown in FIG. 7
   λmax 363, 382, 405
4) $^1$H-NMR (measured in DMSO-d$_6$): shown in FIG. 8
   δ9.20 ppm (bd), 7.65 (d, J=8.65, aromatic-H), 6.54 (d, J=8.58, aromatic-H), 3.64 (s, methyl ester)

Example 5

Preparation of V-28-3M

To 1,500 ml of a dimethyl sulfoxide-methanol mixed solvent (mixing ratio 9/2) containing 25.8 g (19.3 mmol) of N-(9-fluorenylmethoxycarbonyl)-V-28-3M prepared by the method in Example 2, 150 ml of 28% aqueous ammonia (10 v/v % based on the reaction solution) was added at 25° C., followed by stirring for 2 hours to obtain a reaction solution containing 17.8 g of the title compound with a yield of 82%. This reaction solution was cooled under ice cooling, and 3,000 ml of water was added thereto to obtain a slurry of the thus precipitated title compound. The title compound was separated from the slurry and suspended in 1.5 L of isopropyl alcohol, and the suspension was stirred at 25° C. for 17 hours. The title compound was separated from the isopropyl alcohol slurry and dried to obtain 29.6 g of crude V-28-3M as a brown solid (V-28-3M content, 60.3%).

The by-product D contained in the crude V-28-3M was reduced to its detection limit or less via a purification step.

Also, the physicochemical data of the title compound obtained by this method coincided with those of V-28-3M described in JP-A-3-81225, and the same result was also obtained regarding its antimycotic activity.
1) Appearance: yellow powder
2) Mass spectrometry: MS (FAB+); m/z 1127.7 (MH$^+$)
3) Results of the measurement of ultraviolet absorption spectrum (measured in MeOH) and $^1$H-NMR (measured in DMSO-d$_6$) coincided with those described in JP-A-3-81225.
   δ7.66 ppm (d, J=8.67 Hz, aromatic-H), 6.55 (d, J=8.61, aromatic-H), 3.62 (s, methyl ester)

Example 6

Preparation of V-28-3M

To 2.3 ml of a reaction solution containing 37 mg of N-trifluoroacetyl-V-28-3M prepared by the method in Example 4, 2.2 ml of 28% aqueous ammonia was added at 20° C., followed by stirring for 94 hours to obtain 4.5 ml of a reaction solution containing 23 mg of the title compound with a yield of 68%. This reaction solution was cooled in an ice bath, 8 ml of water was added thereto to obtain a slurry, and then the title compound was separated to obtain 65.0 mg of crude V-28-3M as a brown solid (content, 21%).

Example 7

Preparation of N-benzylidene-V-28-3M

In 18 ml of dimethyl sulfoxide, 413 mg (0.17 mmol) of crude V-28-3 was dissolved, 0.2 ml of benzaldehyde (5 mol equivalents based on V-28-3) was added thereto at room temperature, followed by stirring at room temperature for 3 hours. To the reaction solution, potassium carbonate (3 mol equivalents based on V-28-3) was added, and then methyl p-toluenesulfonate (5 mol equivalents based on V-28-3) was added, followed by stirring under ice cooling for 3 hours to obtain a reaction solution containing 186 mg of N-benzylidene-V-28-3M with a yield of 90%.

Molecular weight: 1215 (mass spectrometry: MS (FAB+); 1215.6 (MH$^+$))

When a 50 mM phosphate buffer (pH 4. 0) was added to the thus obtained reaction solution containing N-benzylidene-V-28-3M for a deprotection reaction, N-benzylidene-V-28-3M was quickly converted into V-28-3M.

Comparative Example 1

Preparation of N-(9-fluorenylmethoxycarbonyl)-V-28-3M using methyl iodide

In 1,500 ml of dimethyl sulfoxide-methanol (mixing ratio 9:2, volume ratio), 53.0 g (20.14 mmol) of crude N-(9-fluorenylmethoxycarbonyl)-V-28-3 obtained by the method in Example 1 was dissolved at room temperature. This solution was cooled in an ice bath, and 2.78 g of potassium carbonate and 25.1 ml of methyl iodide were added thereto, followed by stirring under ice cooling. After 2.5 hours, the reaction solution was returned to room temperature and unreacted methyl iodide was evaporated under a reduced pressure to obtain a reaction solution containing 25.2 g of the title compound with a yield of 93%. The title compound was used in the following deprotection reaction step without isolating it from the solution.

In this method, the formation ratio of the Fmoc-protected by-product D was 5.7 area % (based on Fmoc V-28-3M, HPLC analysis) which was larger than that in Example 2. Also, when its purification was carried out in the same manner as described in Example 5, the by-product D in the original compound (V-28-3M) was found to be 7.7 area % (based on V-28-3M, HPLC analysis) which was larger than that in Example 5. This result seems to be due to poor selectivity of the by-product D because of the large amount of contaminated by-product D.

Industrial Applicability

Since the methyl esterification method of the present invention is efficient and uses methyl methanesulfonate or methyl p-toluenesulfonate having lower dangerous than conventionally used diazomethane or trimethylsilyldiazomethane, it is excellent as an industrial production method of the antimycotic agent V-28-3M.

Additionally, when methyl methanesulfonate or methyl p-toluenesulfonate is used in the methyl esterification, by-production of the by-product D can be controlled at a lower level than the case where methyl iodide is used as the methyl esterification agent, so that it is markedly useful in the production process of medicaments.

What is claimed is:

1. A process for preparing V-28-3M represented by formula (4):

Formula (4):

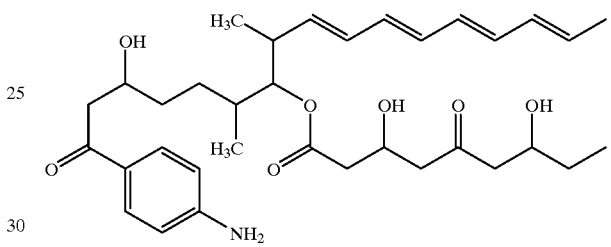

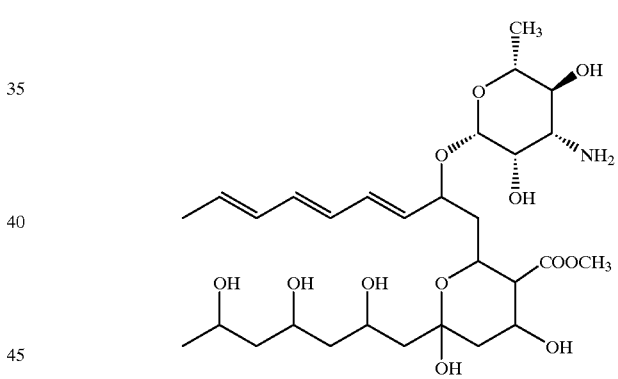

comprising reacting an N-protected form of V-28-3 represented by formula (1):

Formula (1):

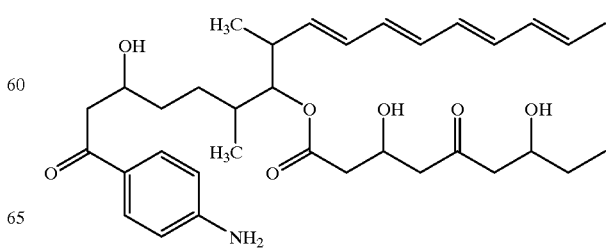

-continued

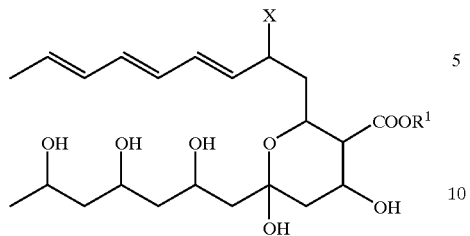

wherein R¹ represents a hydrogen atom, and X represents formula (2) or formula (3):

Formula (2):

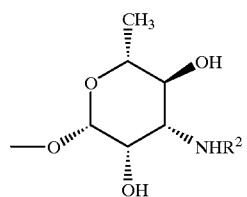

wherein in formula (2) R² represents a 9-fluorenylmethoxycarbonyl group or a trifluoroacetyl group;

Formula (3):

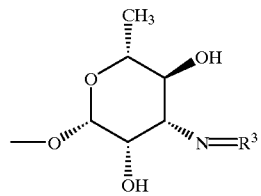

wherein in formula (3) R³ represents a benzylidene group; with methyl methanesulfonate or methyl p-toluenesulfonate in the presence of a base for methyl esterification of the carboxyl group of the N-protected compound to produce a methyl ester of N-protected V-28-3 represented by formula (1) wherein R¹ represents a methyl group, and X represents formula (2) or formula (3); and releasing the N-protected group from the protected compound.

* * * * *

UNITED STATES PATENT AND TRADEMARK OFFICE
CERTIFICATE OF CORRECTION

PATENT NO.    : 6,346,610 B1
DATED         : February 12, 2002
INVENTOR(S)   : Kataoka et al.

It is certified that error appears in the above-identified patent and that said Letters Patent is hereby corrected as shown below:

<u>Title page,</u>
Item [73], should read:

-- [73]  Assignee:      Ajinomoto Co., Inc., Tokyo (JP) --

Signed and Sealed this

Twentieth Day of August, 2002

Attest:

JAMES E. ROGAN
*Attesting Officer*    *Director of the United States Patent and Trademark Office*